United States Patent [19]

Paul

[11] Patent Number: 4,775,793
[45] Date of Patent: Oct. 4, 1988

[54] METHOD FOR DETERMINING CHELATED FERRIC ION CONCENTRATION

[75] Inventor: James M. Paul, DeSoto, Tex.

[73] Assignee: Mobil Oil Corporation, New York, N.Y.

[21] Appl. No.: 838,848

[22] Filed: Mar. 12, 1986

[51] Int. Cl.[4] .............................................. G01J 3/36
[52] U.S. Cl. ..................................... 250/373; 250/372
[58] Field of Search ............................... 250/373, 372

[56] References Cited

U.S. PATENT DOCUMENTS

| | | | |
|---|---|---|---|
| 3,959,249 | 5/1976 | Antonini | 530/368 |
| 4,189,462 | 2/1980 | Thompson . | |
| 4,388,293 | 6/1983 | Diaz . | |
| 4,499,059 | 2/1985 | Jones et al. . | |

FOREIGN PATENT DOCUMENTS

| | | | |
|---|---|---|---|
| 82.30861.4 | 8/1983 | European Pat. Off. . | |
| 572686 | 1/1975 | U.S.S.R. | 250/373 |

OTHER PUBLICATIONS

Willard et al., "Instru. Methods of Analy." p. 88 (1974).

Primary Examiner—Janice A. Howell
Assistant Examiner—Richard Hanig
Attorney, Agent, or Firm—Alexander J. McKillop; Michael G. Gilman; Stanislaus Aksma

[57] ABSTRACT

A method of determining the concentration of a chelated ferric ion in a solution comprising measuring the ultraviolet (UV) light absorption of the solution at the wavelength of about 237 to about 241 nanometers (nm). The measured absorption is then correlated to a previously-determined value of the chelated ferric ion for the measured UV absorption value.

8 Claims, 1 Drawing Sheet

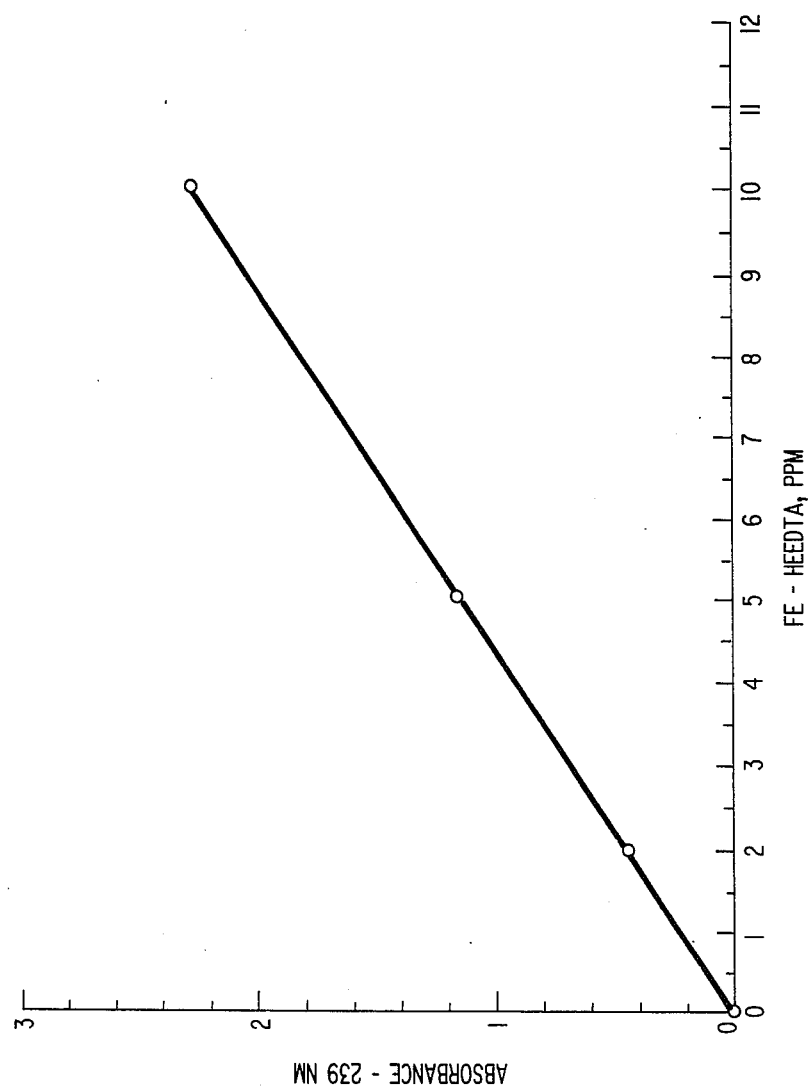

METHOD FOR DETERMINING CHELATED FERRIC ION CONCENTRATION

BACKGROUND OF THE INVENTION

1. Field of the Invention

The present invention relates to a method for measuring the concentration of chelated ferric ions in a solution, especially in a process solution.

2. Description of the Prior Art

There are a number of chemical processes requiring efficient, fast and reliable methods of measuring the concentration of chelated ferric ions in process solutions. One of such processes involves the removal of hydrogen sulfide ($H_2S$) from a gaseous stream by contacting the stream with a polyvalent metal chelate solution, e.g., iron chelate solution, to oxidize the $H_2S$ to elemental sulfur, e.g., see Snavely et al EPA No. 82306861.4, filed Dec. 22, 1982, published under Publication No. 0 086 919 on Aug. 31, 1983, the entire contents of which are incorporated herein by reference.

In the method of Snavely et al, hydrogen sulfide is selectively removed from a gas containing carbon dioxide ($CO_2$) and the $H_2S$ in an oxidation-reduction system by contacting the hydrogen sulfide-containing gas stream with a solution of a polyvalent cation, such as iron, complexed with a chelating agent, such as ethylenediaminetetraacetic acid or sodium salt thereof. In such a process, iron in the ferric state ($Fe^{+++}$) oxidizes the hydrogen sulfide to sulfur, the iron is reduced to the ferrous state ($Fe^{++}$), and the solution is subsequently regenerated by aeration to convert the iron to the ferric state. The sulfur is recovered from the solution by froth flotation.

However, in spite of the cyclic nature of the process and its regeneration cycle, the iron/chelating agent complex degrades causing iron to precipitate, thereby lowering the efficiency of the hydrogen sulfide removal process. Accordingly, iron-chelate complex or free chelating agent must be added to the process loop to maintain a constant level of reactive iron available to remove the $H_2S$. The amount of iron must be maintained within relatively narrow limits (e.g., 2500 ppm) depending on the composition of the incoming gas stream and the pH of the process solution. Several methods have been proposed heretofore to monitor the concentration of iron chelate in process solutions. Such methods include analytical methods, e.g., potentiometric, photometric, precipitation analysis and dye end-point titrations. Some of these methods perform relatively well in relatively physically clean solutions of pure compounds, but they are not sufficiently reliable in process solutions containing a multitude of potentially interfering ions, e.g., thiosulfate ($S_2O_3^=$), sulfate ($SO_4^=$), sodium ($Na+$), carbonate ($CO_3^=$), sulfide ($S^=$) ions. Such process solutions may also be deeply colored. They also may contain suspended solids, such as sulfur ($S°$) and iron hydroxides, $[Fe(OH)_x]$, wherein $X=2$ or 3. The coloration and the suspended solids may also interfere with the efficacy of the previously-used iron chelate quantifying methods.

Accordingly, it is a primary object of the present invention to provide a method of determining the concentration of a ferric ion in process solutions.

Additional objects of the invention will become apparent to those skilled in the art from the following specification and the attached claims.

SUMMARY OF THE INVENTION

A method of determining the concentration of a ferric chelate ($Fe^{+++}$) in a solution comprises subjecting the solution to ultraviolet (UV) light radiation at the wavelength of about 237 to about 241 nanometers (nm), measuring the UV absorption of the solution, and then correlating the UV absorption to a previously-determined value of the ferric chelate concentration for the measured absorption. The thus-determined value of the ferric chelate concentration can be utilized to control the amount of the ferric chelate or of a chelate added to the process solution.

BRIEF DESCRIPTION OF THE FIGURE

The FIGURE illustrates the UV absorption of ferric chelated ion with 2-hydroxy ethylethylene diamine triacetic acid (Fe-HEEDTA) as a function of concentration thereof.

DETAILED DESCRIPTION OF THE INVENTION

The ultraviolet light absorption is measured by any suitable means, e.g., a spectrophotometer operating in the UV spectrum at about 200 to about 400 nm. The solution is subjected to ultraviolet light radiation at the wavelength of about 237 to about 241, preferably about 238 to about 240, and most preferably at about 239 nm, since at the wavelength of about 239 nm, the ferric chelate exhibits the maximum absorption. If it is desired to control the amount of the chelate in the solution, the absorption is correlated to the concentration of iron-chelate on the curve of UV light absorption as a function of iron-chelate concentration, derived in any convenient manner, e.g., by plotting the UV absorption of standard solutions of iron chelate as a function of known concentrations of the iron chelate in the standard solutions. Subsequently, if needed, the required amount of iron chelate or a free chelating agent is added to the solution to bring the concentration of the ferric ion to the required level. The free chelating agent can be added to the solution to increase the ferric chelate concentration since, it is believed, it will redissolve the precipitated iron hydroxides, thereby forming additional iron chelate. The UV absorption is linear for the ferric ion-chelate concentration of from 0 to 10 parts per million (ppm). The process of Snavely et al operates in this region of the ferric ion-chelate concentration and therefore a standard calibration curve for a process of Snavely et al can be conveniently prepared by making several standard solutions of the iron-chelate compound and measuring the absorption thereof in the UV spectrum.

The UV spectrophotometer is operated at the wavelength ranges specified above, i.e., about 237 to about 241 nm, preferably about 238 to about 240 and most preferably about 239 nm, for determining the concentration of iron chelated with any of the chelating agents identified below. It will be apparent to those skilled in the art that a curve correlating the absorption to the ferric ion concentration for a given ferric ion concentration-chelate complex can be used to determine the ferric ion concentration in a ferric ion-chelate complex wherein any other chelating agent is used, since the molar ratio of ferric ion to the chelating agent in most of such complexes is 1:1.

The iron-chelate solutions employed in the process of the invention are coordination complexes in which the iron metal ions form chelates with amino acids having one of the following general formulae:

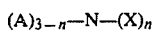  (I)

wherein
n is a number from 1 to 3;
X is selected from the class consisting of acetic and propionic acid groups;
A is 2-hydroxy ethyl, 2-hydroxy propyl, or an alkyl group having from 1 to about 4 carbon atoms; or

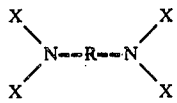  (II)

wherein
R is ethylene, propylene or isopropylene or, alternatively, cyclohexane or benzene, where the two hydrogen atoms replaced by nitrogen are in the 1,2-position;
from two to four of the groups X are selected from the class consisting of acetic and propionic acid groups; and,
from zero to two of the groups X are selected from the class consisting of 2-hydroxy ethyl, 2-hydroxy propyl and

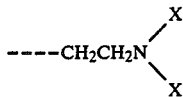

The iron chelates are readily formed in aqueous solutions by the reaction of an appropriate salt, oxide or hydroxide of the iron and chelating agent in the acid form or an alkali metal or ammonium salt thereof. Exemplary chelating agents include: amino acetic acids derived from ammonia or 2 hydroxy alkylamines, such as glycine, diglycine (amino diacetic acid), NTA (nitrilo triacetic acid), 2-hydroxy alkyl glycine; di-hydroxyalkyl glycine, and hydroxyethyl or hydroxypropyl diglycine; amino acetic acids derived from ethylene diamine, diethylene triamine, 1,2-propylene diamine, and 1,3-propylene diamine, such as EDTA (ethylene diamine tetraacetic acid), HEEDTA (2-hydroxy ethylethylene diamine triacetic acid), DETPA (diethylene triamine pentaacetic acid); amino acetic derivatives of cyclic 1,2-diamines, such as 1,2-diamino cyclohexane-N, N-tetraacetic acid, and the amides of polyamino acetic acids disclosed in U.S. Pat. No. 3,580,950 to Bersworth, the entire contents of which are incorporated herein by reference. Preferred chelating agents are ethylenediaminetetraacetic and N-(2-hydroxy-ethyl) ethylenediamine triacetic acids, and the most peferred chelating agent is N-(2-hydroxy-ethyl) ethylenediamine triaacetic acid because of its pH tolerance.

The invention is particularly useful in measuring the amount of chelated ferric ions in impure process solutions containing, in addition to the ferric, and possibly, ferrous ions, other impurities, such as thiosulfate ($S_2O_3^=$), sulfate ($SO_4^=$), sulfide ($S^=$), sodium ($Na+$), carbonate ($CO_3^=$) and/or bicarbonate ($HCO_3^-$) ions. Previously proposed methods for determining the concentration of chelated ferric ions in such impure solutions, such as photometric, precipitation determinations and dye endpoint titrations, do not give an accurate and reliable indication of the chelated ferric ion concentration in the process solutions because, it is believed, of the deeply colored process solutions and the presence of precipitates of sulfur ($S°$) and iron hydroxides [$Fe(OH)_x$] wherein $x=2$ or 3.

It will be apparent to those skilled in the art, that the process solution can be sampled at any convenient point in the process to measure the chelated ferric ion concentration thereof. After a sample of the solution is passed through a spectrophotometer to obtain an absorption value, it can be correlated to the chelated ferric ion concentration corresponding thereto from a previously-obtained calibration curve of the absorption at a given wavelength to the chelated ferric ion concentration.

For optimum results, it is preferred to sample the process solution at a point in the process wherein the concentration of the chelated ferric ion is or should be the highest. Thus, for example, in the process of Snavely et al (see European Patent Application No. 82306861.4) the preferred point for sampling the process solution is just upstream of the mixers 20 (FIG. 1 of Snavely et al). It is important for the purposes of the present invention that the solution being tested for UV absorption does not contain excessive amounts of chelated ferrous ion ($Fe++$) since excessive ferrous ion concentration may have adverse effect on the UV absorption spectrum of the chelated ferric ion because UV light is absorbed in the similar wavelength by the ferrous and the ferric chelates. The maximum amounts of the chelated ferrous ion which may be present in the solution are unknown at this time. However, it is estimated that chelated ferrous ion can be present in the solution in the amount of up to 2% of the amount of the chelated ferric ion without causing undue interference with the absorption of the UV light by the chelated ferric ion in the solution.

It will be apparent to those skilled in the art that the process of this invention is applicable to any process wherein it is desired and/or necessary to monitor and/or adjust the amount of the chelated ferric ion in a process stream. Thus, the instant process can be used to monitor and/or adjust the chelated ferric ion concentration in the processes of Snavely et al (EPA No. 82306861.4) or Thompson et al, U.S. Pat. No. 4,189,462, also disclosed by Cabodi et al in *Oil and Gas Journal*, July 5, 1982, pages 107–110, the entire contents of all of which are incorporated herein by reference.

Any UV spectrophotometer may be used in the process of the present invention. However, it is important to use quartz cuvettes to avoid interference in the UV region by extraneous absorbing materials, e.g., plastic or impurities.

The following Examples further illustrate the essential features of the invention. However, it will be apparent to those skilled in the art that the specific reactants and reaction conditions used in the Examples do not limit the scope of the invention.

EXAMPLE

A UV/VIS spectrophotometer, Model 8450A, manufactured by Hewlett-Packard, was operated at a wavelength of 239 nanometers (nm). The instrument was zeroed against distilled water, and all standards and unknown samples were referenced against water. Quartz cuvettes were used to avoid interference in the UV region with extraneous absorbing material. Standard samples were prepared by diluting a fresh solution used in the process described by Snavely et al. The fresh Versenol AG 5% Fe solution obtained from the Dow Chemical Company, containing 50,000 ppm of ferric chelate was diluted with distilled water in a 20:1 ratio to obtain a solution containing 2500 ppm of ferric chelate. The dilution was carried out at pH of 7.15, and adjusted with sodium carbonate. The dilution of the solution was necessary because of the relatively limited operating range of the spectrophotometer used in this Example. The upper operating range of the instrument was the absorption value of slightly higher than 2.0, which corresponds to the chelated ferric ion concentration of about 10 ppm.

Three standard solutions were prepared by diluting the fresh process solution with distilled water by the amounts indicated below to obtain the solutions having the chelated ferric ion concentration indicated in the parenthesis:

(1) dilution factor of 250 (10 ppm);
(2) dilution factor of 500 (5 ppm);
(3) dilution factor of 1250 (2 ppm);

The absorption of the three standard solutions was then tested at 239 nm in the spectrophotometer and the absorption of the three samples was plotted as a function of the chelated ferric ion concentration to obtain the linear curve shown in the FIGURE.

1 ml of a liquid process stream conducted from the regeneration cells 44 or 46 (FIG. 1 of Snavely et al), was obtained from the process line just before the introduction of the stream into the static mixer 20. The sample was diluted with 1000 ml of distilled water and then subjected to analysis in the spectrophotometer described above. The spectrophotometer yielded the absorption value of 0.84, indicating the chelated ferric ion concentration of 3,671 ppm (0.066M). Accordingly, fresh Versenol AG 5% Fe or a free chelate could be added to increase the iron activity, if needed.

It will be apparent to those skilled in the art that the specific embodiments discussed above can be successfully repeated with ingredients equivalent to those generically or specifically set forth above and under variable process conditions.

From the foregoing specification, one skilled in the art can readily ascertain the essential features of this invention and without departing from the spirit and scope thereof can adapt it to various diverse applications.

I claim:

1. A method for determining the concentration of a chelated ferric ion selected from the group consisting of the chelated iron compounds of ethylenediaminetetraacetic acid and N-(2-hydroxy-ethyl)ethylenediamine triacetic acid in an impure process solution containing impurities selected from the group consisting of the ion of thiosulfate, sulfate, sulfide, sodium, carbonate, bicarbonate and chelated ferrous ions, precipitates of sulfur (S°) and iron hydroxides of the formula $Fe(OH)_x$, wherein $x=2$ or 3, and the amount of chelated ferrous ion which is 2% or less of the amount of the chelated ferric ion in the solution, the method comprising measuring the ultraviolet (UV) light absorption of the solution at the wavelength of about 237 to about 241 nanometers (nm) and correlating the measured absorption to a previously-determined value of the chelated ferric ion concentration for the measured absorption.

2. A method of claim 1 wherein the UV absorption of the solution is measured at the wavelength of about 238 to about 240 nm.

3. A method of claim 2 wherein the UV absorption of the solution is measured at the wavelength of about 239 nm.

4. A method of claim 3 wherein the chelated ferric ion is a product containing 1:1 molar ratio of iron and N-(2-hydroxy ethyl) ethylenediamine triacetic acid.

5. In a process of selectively removing hydrogen sulfide ($H_2S$) from a gaseous stream comprising the $H_2S$ and carbon dioxide ($CO_2$), comprising contacting the gaseous stream with an iron chelate solution for a sufficient time to allow the iron chelate to oxidize the $H_2S$ to elemental sulfur while reducing the iron from ferric to ferrous ion, and subsequently regenerating the solution by oxidizing the ferrous ion to ferric ion, without allowing the solution to absorb appreciable amounts of the $CO_2$, an improvement comprising determining the concentration of a chelated ferric ion in an impure process solution containing impurities selected from the group consisting of the ions of thiosulfate, sulfate, sulfide, sodium, carbonate, bicarbonate and chelated ferrous ions, precipitates of sulfur (S°) and iron hydroxides of the formula $Fe(OH)_x$, wherein $x=2$ or 3, and the amount of a chelated ferrous ion which is 2% or less of the amount of the chelated ferric ion in the solution, the chelated ferric ion being selected from the group consisting of the compounds of ethylenediaminetetraacetic acid and N-(2-hydroxy-ethyl) ethylenediamine triacetic acid, by measuring the ultraviolet (UV) light absorption of the solution at the wavelength of about 237 to about 241 nanometers (nm) and correlating the measured absorption to a previously-determined value of the chelated ferric ion concentration for the measured absorption.

6. A process of claim 5 wherein the UV absorption of the solution is measured at the wavelength of about 238 to about 240 nm.

7. A process of claim 6 wherein the UV absorption of the solution is measured at the wavelength of about 239 nm.

8. A process of claim 7 wherein the chelated ferric ion is a product containing 1:1 molar ratio of iron and N-(2-hydroxy ethyl) ethylenediamine triacetic acid.

* * * * *